(12) United States Patent
Zak et al.

(10) Patent No.: US 10,386,280 B2
(45) Date of Patent: Aug. 20, 2019

(54) DEVICE FOR MEASURING SHEAR PROPERTIES OF ASPHALT MIXTURES

(71) Applicants: CZECH TECHNICAL UNIVERSITY IN PRAGUE, FACULTY OF CIVIL ENGINEERING, Prague (CZ); THE REGENTS OF THE UNIVERSITY OF CALIFORNIA, Oakland, CA (US)

(72) Inventors: Josef Zak, Prague (CZ); John Harvey, Davis, CA (US); James Signore, Richmond, CA (US)

(73) Assignees: CZECH TECHNICAL UNIVERSITY IN PRAGUE, FACULTY OF CIVIL ENGINEERING, DEPARTMENT OF ROAD STRUCTURES, Prague (CZ); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/742,059

(22) PCT Filed: Jun. 21, 2016

(86) PCT No.: PCT/CZ2016/050019
§ 371 (c)(1),
(2) Date: Jan. 5, 2018

(87) PCT Pub. No.: WO2017/005229
PCT Pub. Date: Jan. 12, 2017

(65) Prior Publication Data
US 2018/0202911 A1   Jul. 19, 2018

(30) Foreign Application Priority Data
Jul. 9, 2015   (CZ) .................................... 2015-486

(51) Int. Cl.
*G01N 3/00* (2006.01)
*G01N 3/24* (2006.01)
*G01N 3/04* (2006.01)

(52) U.S. Cl.
CPC ................. *G01N 3/24* (2013.01); *G01N 3/04* (2013.01); *G01N 2203/0025* (2013.01);
(Continued)

(58) Field of Classification Search
CPC .... G01N 3/24; G01N 3/04; G01N 2203/0025; G01N 2203/0222; G01N 2203/0274; G01N 2203/0435
(Continued)

(56) References Cited

U.S. PATENT DOCUMENTS 2,831,096 A * 4/1958 Signore, Jr. ........... B29B 13/023
                                                        219/385
5,119,681 A   6/1992 Miszczak
(Continued)

FOREIGN PATENT DOCUMENTS

CN   203025051   6/2013
FR   2557296     6/1985

OTHER PUBLICATIONS

International Search Report (dated Nov. 4, 2016) for corresponding International App. PCT/CZ2016/050019.

*Primary Examiner* — Max H Noori
(74) *Attorney, Agent, or Firm* — WRB-IP LLP

(57) ABSTRACT

A device for measuring shear properties of asphalt mixtures includes a machine for testing the material strength, equipped with an operational frame, fixing elements and driving mechanism, the machine including a steel socket equipped at at least one of a bottom and a top edge thereof with an inner flange to accommodate a testing specimen, the testing specimen having a central open hole, and a steel (Continued)

insert adapted to be inserted into the open hole in the testing specimen, the steel insert being equipped with a rim at at least one of an end thereof at the top edge of the steel socket and at end thereof at the bottom of the steel socket, while a size of a clearance between the inner flange and the rim being between 5 to 60 mm, and the steel insert being equipped with elements for fixing to clamping elements of the device, and measuring probes being connected to the steel insert.

5 Claims, 3 Drawing Sheets

(52) U.S. Cl.
CPC ............ *G01N 2203/0222* (2013.01); *G01N 2203/0274* (2013.01); *G01N 2203/0435* (2013.01)

(58) Field of Classification Search
USPC .......................................................... 73/841
See application file for complete search history.

(56) References Cited

U.S. PATENT DOCUMENTS

| | | | | |
|---|---|---|---|---|
| 6,929,393 B1* | 8/2005 | Brock | ................ | B07B 1/46 |
| | | | | 366/140 |
| 2014/0026635 A1* | 1/2014 | Zorn | ................ | G01N 3/24 |
| | | | | 73/12.06 |

* cited by examiner

DEVICE FOR MEASURING SHEAR PROPERTIES OF ASPHALT MIXTURES

BACKGROUND AND SUMMARY

The invention deals with a device for measuring shear properties of asphalt mixtures containing a machine for testing the material strength, especially for tests of tensile, compression, flexural and shear strengths, which is equipped with an operational frame, fixing elements and driving mechanism. The device is suitable in particular for determining the roadways asphalt mixtures resistance to the occurrence of permanent deformations in the form of ruts.

When designing a roadway, an important part of the design is to determine the resistance to traffic-induced permanent deformations, such as ruts. A wavy surface decreases the transportation quality and prevents water drainage, which compromises the adhesion of a vehicle's tire to the roadway pavement. This results in lower area involved in braking effect and increases the risk of aquaplaning. The engineering task therefore is to minimize the risk of occurrence of permanently deformed pavement by the most accurate prediction possible and by monitoring of such occurrence, which would allow for proper suggestions or timely actions in reconstructing a roadway.

Permanent deformations of asphalt compacted layers of a roadway pavement caused by the traffic load are attributed to shear tension in the roadway and to the accompanying shear flow. These effects are described in detail for example in Symplectic Engineering Corporation 1999; Deacon et al. 2002; Monismith et al. 1994. Shear properties of materials like asphalt mixtures are measured by two currently known types of devices. The first one is the Superpave Shear Tester/SST/developed at the University of California, Berkeley, in the nineties. The second device is the Double Shear Tester/DST/, which was developed at the Université de Limonges in 2006.

Tests used at present to estimate the mixture predisposition to fail prematurely are either not very accurate, or they require to purchase expensive testing equipment (SST).

Current practice, except for the U.S.A. and Canada, normally predicts the permanent deformation upon information about the measured change of the material in volume (using so-called Hamburg-Wheel Tracking Device). In case of well-compacted mixture it however was proved that the shear tension has significantly greater impact on forming the permanent deformations than the change in volume. But at present, the shear tension measurement with sufficient accuracy is only possible with the expensive so-called SST equipment, which therefore is unobtainable for many laboratories.

Test methods used at present vary significantly with respect to their extent, ability to predict the pavement performance with sufficient accuracy and the input data they use. Most of these tests are empiric-based and as such they were developed with the presumption of certain traffic and climatic conditions based on experience. One of these methods setbacks is the fact that they cannot be used for the roadways construction design calculations.

There exist a number of relevant patents of Chinese origin (CN203745314 (U), CN203350137 (U), CN103245571 (A), CN103267686 (A), CN103245571 (A)). However no protected solution was found that would be identical to the present one. The topic of measuring properties of compacted asphalt mixtures is discussed also in utility design number 2011-24012 registered at the ÚPV ČR (Industrial Property Office of the Czech Republic). This device however is designed for measuring the friction between the asphalt mixture and steel as the input properties for numeric calculations describing especially in-vitro testing. The device does not allow to measure shear properties of asphalt mixtures.

As the existing solution used for measuring the shear properties in the U.S.A. can be considered the device called SuperPave Shear Tester (SST). Disadvantages of this existing solution may be summarized in the following points. Firstly, the specimen must be glued to two steel bases, which serve for fixing the specimen in the testing device. Quality of glued joint varies largely, it depends on kind of used glue and experience and meticulousness of technician making the glued joint. It means that not only such process of gluing makes the testing more expensive and longer but since the glued joint quality varies, this process introduces yet another variable quantity into the measured in-vitro results, thus increasing the standard deviation of measurements.

Disadvantages of the present solutions can be summed up into the following points. Many devices require that part of the testing device or the sample itself were glued or bonded. Using glue makes the testing procedure longer and more expensive. Likewise, measured values are affected by the quality of the bond workmanship.

With the current solutions, the shear tension is not applied in the same direction, in which the samples are produced or compacted on a roadway, meaning that the load impact direction does not correspond to the actual conditions on roadways. This fact is critical for determination of parameters that are subsequently used in calculation of the asphalt roadways durability.

Another disadvantage is that the standard UTM equipment cannot be used in the testing procedure plus the preparation of the testing specimens is complex.

Existing solutions do not allow to apply cross-tension or they apply the cross-tension in inadequate values. They further do not allow to measure the cross-tension during testing. Existing solutions do not allow to test specimens obtained by the standard boring technology from the pavements.

For some devices, the measured values are distorted by application of clamping or contact pressures.

According to an aspect of the invention, a device is provided for measuring shear properties of asphalt mixtures containing a machine for testing the material strength, especially for tests of tensile, compression, flexural and shear strengths, which is equipped with an operational frame, fixing elements and driving mechanism, according to this invention. Its principle is that it contains a steel socket equipped at its bottom and/or at its top edge with an inner flange to accommodate the testing specimen that is equipped with a central open hole in it, and further it contains a steel insert that can be inserted into an open hole through the testing specimen, equipped at its end at the top edge of the socket and/or at its end at the socket bottom with a rim. The clearance between the inner flange and the rim is adjustable from 5 to 60 mm and the steel insert is equipped with elements for fixing to the clamping elements of the testing device. Also, measuring probes are connected to the steel insert.

Advantageously, flexible material is inserted below the steel insert rim. In one preferred embodiment the steel socket is formed by at least two parts, between which is located a tension meter for measuring the pressure the material applies to the steel socket. The device may be located in a temperature-controlled chamber.

Contact area size between the testing specimen and the inner flange advantageously corresponds to the contact area size between the testing specimen and the steel insert equipped with a rim.

In fact, the testing device is a set-up designed for use in the testing UTMs (Universal Testing Machines), also known as NAT (Nottingham Asphalt Tester). These universal testing devices are commonly used by laboratories focused on roadway materials testing. It means that the set-up is inserted into the UTM and this combination is used to perform the test. The machine contains control and evaluation units, measuring probes, piston driven by the hydraulic or pneumatic unit and temperature-controlled chamber. UST device thus to a certain extent becomes an accessory to the UTM.

Advantages of this device include extremely lower production costs, significantly lower operational costs and approximately half the time needed for preparation of specimens without the need for any other laboratory equipment, i.e. no need for double-edged saw or bonding the specimen to a special base, while it allows to test samples obtained by boring from the roadway as well as in-vitro prepared samples. Another advantage is the simplicity of the testing procedure—without any impacts caused by contact or clamping pressures. Compacted asphalt mixtures are tested in the same direction, in which they are compacted and loaded on the roadway. Using the UST machine for the shear properties testing shows less varied values of some measured parameters. During testing the material is exposed to side tension, which is given by mechanical properties of the tested material itself. Another substantial advantage is also general safety—if the material breaks under the load pressure, it collapses inside the testing set-up.

The advantage of the solution with double-rimmed insert is the option to apply load in both directions, it means from top downwards and from the bottom upwards. In some layers of non-compact roadway pavements the pressure tension changes to tensile tension as the vehicle's wheel rolls over. Therefore, the shear tension direction changes also. Fixing the specimen form both sides allows to simulate this effect in laboratory. We may presume that this kind of fixing will also allow to perform tests of the material resistance against fatigue.

Preliminary analysis of the situation on market revealed that the solution according to the invention has a great potential for practical applications, especially due to higher accuracy of the permanent deformations resistance determination and also because it is very cost efficient. More accurate data about the tested mixture will help avoid premature faults of the roadways and thanks to them the road transportation network administrators will have higher quality information about the roadways actual condition and functionality, which will help them during the construction designs, selection of suitable materials and repairs planning. The device may also be used for measuring even when there are no applicable industrial standards. Since the device according to the invention uses laboratory equipment laboratories already own as a standard, there is no need to create any extra sources for its procurement.

If the device according to the invention is used, it allows to reduce or eliminate the occurrence of permanent deformations by suitable design. This allows for significant savings for the investor and administrator of transportation constructions.

Most laboratories focused on testing the asphalt properties are at present equipped with so-called UTM (Universal Testing Machine, also known as the Nottingham Asphalt Tester (NAT)). This fact is anticipated by the concept of solution according to the invention. When this solution is used the laboratory measurements give the user unambiguous results—functional parameters. When these parameters are known, the mixture composition can be optimized to meet specific needs.

BRIEF DESCRIPTION OF THE FIGURES

The device for measuring shear properties of asphalt mixtures according to this invention will be described in more detail using a specific embodiment examples by means of attached drawings, where FIG. 1 shows the given device in cross-section.

DETAILED DESCRIPTION

Figure 1:
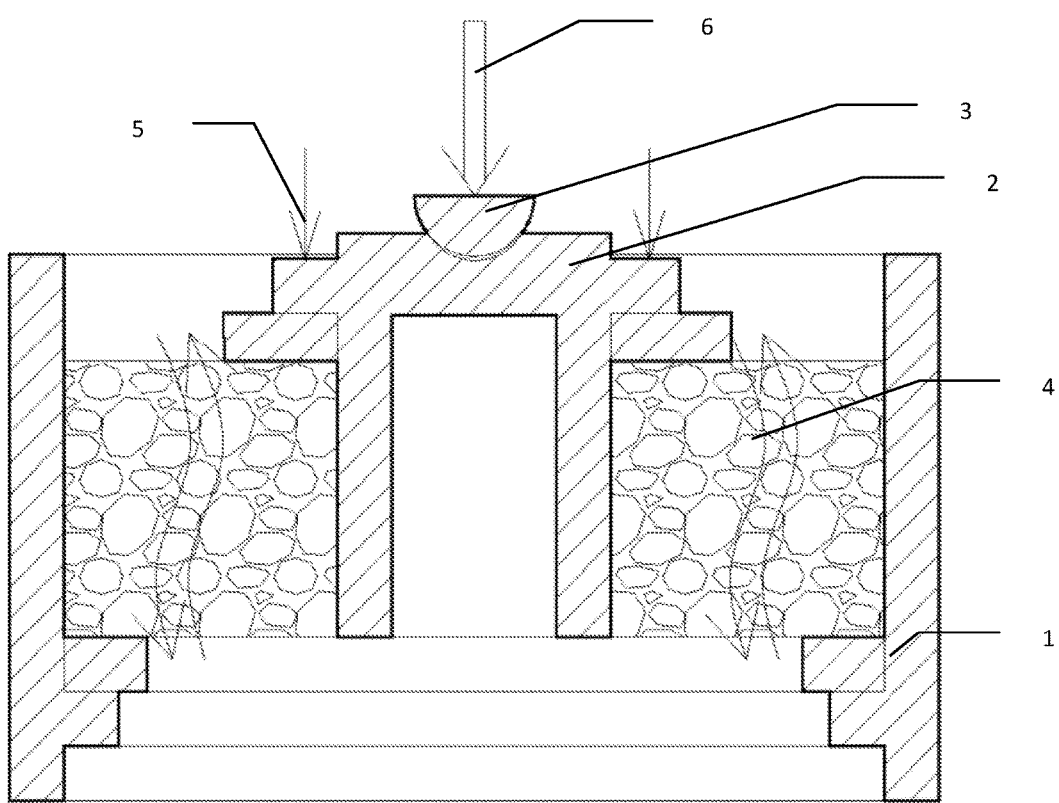
FIG. 1 illustrated a cross-section of the UST example in accordance with the described embodiments.
Figure 2:
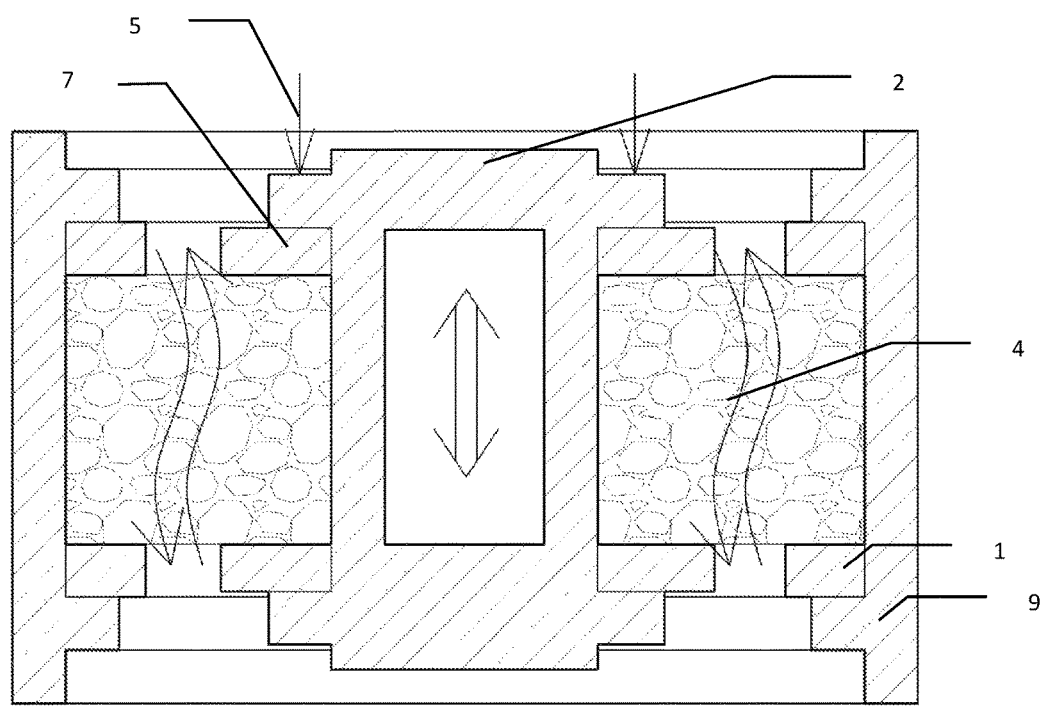
FIG. 2 shows the cross-section of another possible embodiment.
Figure 3:
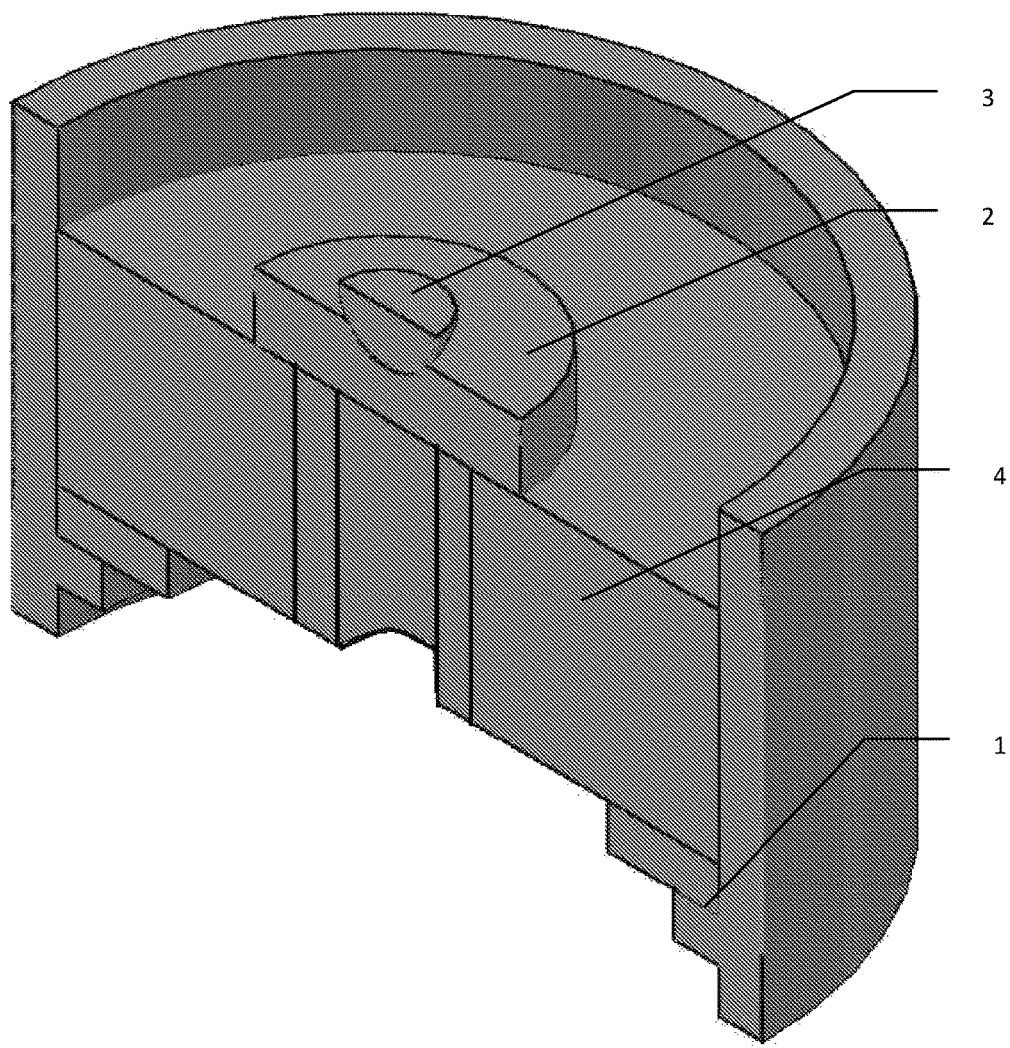
FIG. 3 shows a view of section of one possible embodiments of the device.

Example embodiment of the device for measuring shear properties of asphalt mixtures consists of or comprises a steel socket 9 equipped at its bottom with an inner flange 1 to accommodate the testing specimen 4 with a central open hole in it, and a steel insert 2 that can be inserted into an open hole through the testing specimen 4. The steel insert 2 is equipped with a rim 7 and a clamp 3 for fixing into the testing device. The size of the clearance between the inner flange 1 and the rim 7 can be adjusted from 5 to 60 mm. To the steel insert 2 are connected the measuring probes 5. Below the rim 7 of the steel insert 2 a flexible material 8 is inserted. The device is located in the temperature-controlled chamber.

In another embodiment the steel socket 9 is formed by two parts, between which is located a tension meter measuring the pressure the material applies to the steel socket 9.

The asphalt testing specimen 4, cylindrically shaped with an open hole, is inserted into the steel socket 9 and placed onto its inner flange 1. Inside the testing specimen 4 is inserted the steel insert 2, on which is placed the distribution ball of the clamp 3 of the testing device. To the steel insert 2 are connected the measuring probes 5. Testing procedure consists in or comprise applying controlled load or displacement in direction 6 to the steel insert 2.

Another alternative device for measuring shear properties of asphalt mixtures contains the steel socket 9 equipped at its bottom and the top edge with an inner flange 1 for fixing the testing specimen 4 with the central open hole in it, and the steel insert 2, which can be inserted into the open hole of the testing specimen 4. Steel insert 2 is equipped from both sides with the rim 7 and the place for fixing the loading device. Clearance between the inner flange 1 and the rim 7 can be adjusted from 5 to 60 mm. To the steel insert 2 are connected the measuring probes 5. The device is located in the temperature-controlled chamber.

The asphalt testing specimen 4, cylindrically shaped with an open hole, is inserted into the steel socket 9 and placed onto its inner flange 1. Inside the testing specimen 4 is inserted the steel insert 2. The steel insert 2 is attached to the testing specimen 4 also from the other side than the side it was inserted. Testing specimen 4 is further fixed in the steel socket 9 from the side the steel insert 2 is inserted. Next, the loading device is fixed to the steel insert 2. To the steel insert 2 are connected the measuring probes 5. Testing procedure consists in or comprises applying controlled load or displacement in direction 6 to the steel insert 2.

In case of the alternative solution with the testing specimen 4 fixed both from the top and the bottom side, the fixing of testing specimen 4 is double. The testing specimen 4 is at first fixed to the steel socket 9. On the bottom side the testing specimen 4 is placed onto the inner steel flange 1, which can be manufactured as one monolithic piece with the steel socket 9, or fixed to the steel socket 9 by welding. On the top side, the testing specimen 4 is fixed by the upper steel flange 1. This upper steel flange 1 is fixed to the steel socket 9 for instance by bolts or other connecting system in a way that allows for rectification according to the testing specimen 4 height.

Then the steel insert 2 is fixed to the inner open hole of the testing specimen 4. The steel insert 2 consists of or comprises three parts. The first, upper part is formed by a shank equipped with threads in its part, and a head. This part is placed together with the upper washer to the inner open hole of the testing specimen 4. The lower part is formed by the washer and nut. The washer is put on the shank from below and the washer is tightened to the testing specimen 4. In fact, this design uses fixing the testing specimen 4 with the bolt with two washers. In the head of the insert (bolt) there is a hole with threads to allow fixing of the loading rod of the testing device.

The function of the alternative solution with the testing specimen 4 fixed from both the top and bottom sides is the application of load in both directions. It means the controlled load can be applied in vertical direction both downwards and upwards. Load applied in the form of tension or strain causes shear tension in the testing specimen 4 in alternately changing direction. This effect is similar to shear tensions created in pavement when vehicle's wheel rolls over. Loading the testing specimen 4 in both directions thus allows to simulate loading of the roadway pavement structure. Likewise it is possible to apply shear fatigue test without the impact of accumulated permanent deformation caused by load applied in one direction.

Advantageously this alternative design of the testing device allows to apply sinusoid or other harmonic load in both directions. Loading procedure and measurement of results is the same as for the previous versions.

Common dimensions of the testing specimen 4 are: diameter 150 to 100 mm, height of the specimen 40 to 100 mm, often corresponding to the pavement layer thickness. Steel parts of the device are made of steel with wall thickness 10 to 15 mm. Load application consists in or comprises application of cycles of loading and unloading, so-called cyclical test of strain with unloading, or in application of usually sinusoid waves of load to the testing specimen 4 with frequencies selected from the range 0.1 to 50 Hz. With this kind of loading the response of material is measured. In case of load by strain, tension is measured. In case of load by tension, strain is measured. Results can be evaluated using principles of elasticity, viscoelasticity or possibly viscoelastoplasticity. Measured results include: shear modulus of elasticity, reversible and irreversible function of compliance in shear, number of cycles needed to reach certain level of permanent strain, parameters of rheological models and parameters of models for use in calculation software applications.

The device was used for testing of asphalt compacted mixtures. These mixtures contained conventional, oxidized and polymer-modified asphalt binders. Tests were performed with asphalt compacted mixtures manufactured in California, U.S.A., and in Europe, the Czech Republic. Part of the research project focused also on asphalt compacted mixtures with the content of rubber manufactured in California, U.S.A. It was proved that based on in-vitro measurements the device allows to discern quality between these kinds of materials.

Exemplary procedure of measurement is procurement of testing sample from the pavement by boring or preparation of the testing specimen 4 using gyrator in laboratory. To such testing specimen 4 the central open hole is subsequently bored. This testing specimen 4 is placed into the steel socket 9 and the steel insert 2 is inserted into the open hole of the testing specimen 4. The set-up is placed to the UTM device where to the steel insert 2 are connected the measuring probes 5 and the rod of the loading device is fixed to it. The whole set-up is tempered until the required temperature of the testing specimen 4 is stabilized. Next, testing is performed, i.e. application of load on the testing specimen 4, and its response is evaluated in the form of physical-mechanical properties of tested material.

Device for measuring shear properties of asphalt mixtures will find application in measuring, determining and designing the roadways load capacity when loaded by freight transportation and in determination of the roadways resistance to permanent deformations forming. It uses standard laboratory equipment.

The invention claimed is:
1. Device for measuring shear properties of testing specimens of asphalt mixtures, the device comprising
    a machine for testing material strength the machine comprising
        an operational frame, fixing elements, and a driving mechanism,
        a steel socket equipped at at least one of a bottom and a top edge thereof with an inner flange against which the testing specimen is disposed, the testing specimen having a central open hole, and
        a steel insert adapted to be inserted into the open hole in the testing specimen, the steel insert being equipped with a rim at at least one of an end thereof at the top edge of the steel socket and at, an end thereof at the bottom of the steel socket, wherein a size of a clearance between the inner flange and the rim is between 5 to 60 mm, the steel insert is equipped with elements for fixing to clamping elements of the device, and measuring probes are directly connected to the steel insert.
2. Device according to claim 1, wherein, below the rim of the steel inserts, a flexible material is inserted.
3. Device according to claim 2, wherein the steel socket is formed by at least two parts between which a tension meter is located for measuring a pressure that the material applies to the steel socket.
4. Device according to claim 1, comprising a temperature-controlled chamber in which the steel socket and the steel insert are disposed.
5. Device according to claim 1, wherein a contact area size between the testing specimen and the inner flange corresponds to a contact area size between the testing specimen and the steel insert equipped with a rim.

* * * * *